Sept. 28, 1965 E. S. BOERNER Plant Pat. 2,554
CHRYSANTHEMUM PLANT
Filed June 12, 1964
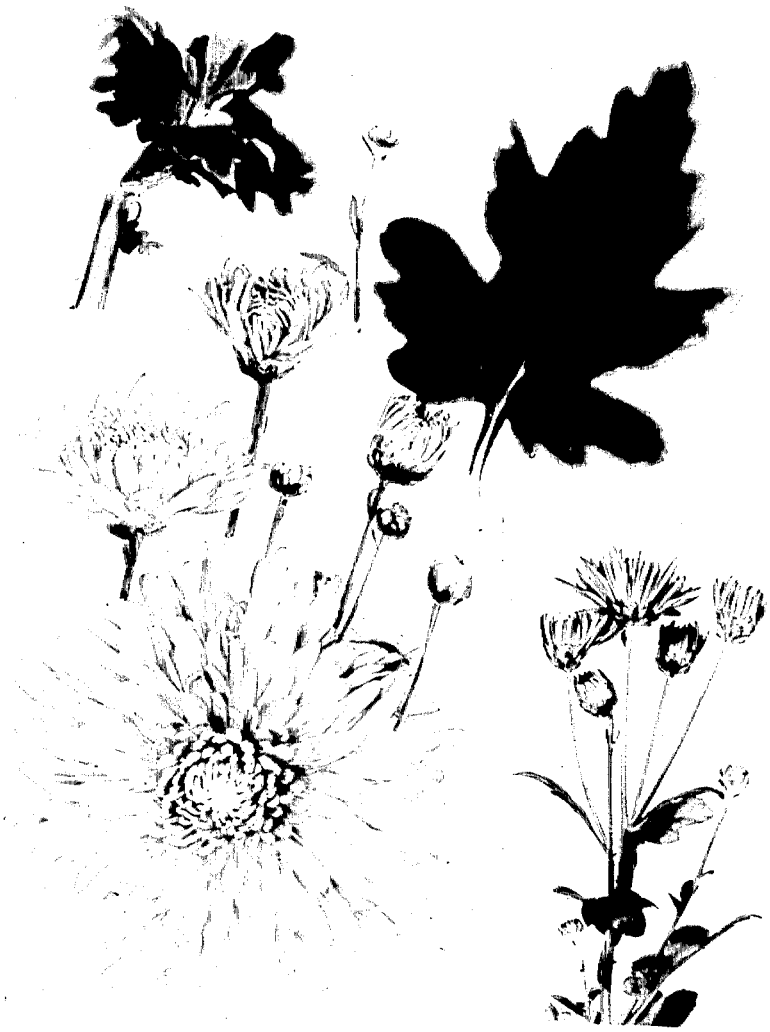
Inventor.
E. S. Boerner
By: Robb & Robb
Attorneys.

United States Patent Office

Plant Pat. 2,554
Patented Sept. 28, 1965

2,554
CHRYSANTHEMUM PLANT

Eugene S. Boerner, Newark, N.Y., assignor to Jackson & Perkins Company, Newark, N.Y., a corporation of New York Filed June 12, 1964, Ser. No. 374,866
1 Claim. (Cl. Plt.—82)

The present invention relates to a new and distinct variety of chrysanthemum plant of the decorative class, which was originated by me by crossing an unnamed and unpatented seedling of "Flicker" (Plant Patent No. 1,465) × "Thrush" (Plant Patent No. 1,168) with the variety "Kingbird" (Plant Patent No. 1,306).

The primary objective of this breeding was to produce a new chrysanthemum variety having the early blooming habit and flower color of the unnamed seedling parent, combined with the vigor and hardiness of the parent variety "Kingbird." This objective was fully achieved, along with other desirable improvements, as evidenced by the following unique combination of characteristics which are outstanding in the new variety and distinguish it from its parents, as well as from all other varieties of which I am aware:

(1) Very vigorous, upright and branching habits of growth;
(2) A relatively early blooming habit;
(3) Very good floriferousness;
(4) Thick flowers;
(5) A distinctive and attractive general color tonality of the flowers corresponding to Scarlet, lightly overcast with Scarlet-Red; and
(6) Good winter hardiness.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen stem which is depicted in black and white for the purpose of illustrating the form and habit of growth of the plant.

The following is a detailed description of the new variety, with color terminology in accordance with Ridgway's Color Standards and Nomenclature:

Parentage: Seedling.
*Seed parent.*—Unnamed seedling of "Flicker" × "Thrush."
*Pollen parent.*—"Kingbird."
Classification: Decorative.
Growth: Very vigorous.
Locations where observations made: Outdoors at Newark, New York, in mid-afternoon during the first part of the month of October.
Cold Resistance: Winter hardy in northern New York State.
Blooming period: From end of September until freezing weather in northern New York State.
Bud:
*Color.*—When petals first divide—Pinkish Buff, Plate 29. When petals begin to unfurl—Coral Red, Plate 13, lightly overcast with Spectrum Red, Plate 1 on the edge of the petal. When half-blown: inside—Scarlet, Plate 1, very lightly overcast with Scarlet-Red, Plate 1. Outside—Light Orange-Yellow, Plate 3, with lower half of petal overcast with Orange, Plate 3.
*Peduncle.*—Color—Cress Green, Plate 31. Strength—strong.
Bloom:
*Size.*—From 5½ inches to 6 inches.
*Stem.*—Strong.
*Form.*—Thick decorative; 3 inches thick.
*Petalage.*—Very double; blooms very floriferous.
*Color.*—Center of flower—Buff-Yellow, Plate 4, lightly overcast with Grenadine Red, Plate 2. Outer petals—Cadmium Orange, Plate 3, overcast lightly with Scarlet, Plate 1. Base of petals—Pale Orange-Yellow, Plate 3. Inside of petals—Scarlet, Plate 1, lightly overcast with Scarlet-Red, Plate 1. Reverse of petals—Pale Orange-Yellow, Plate 3, very lightly overcast with Orange-Buff, Plate 3.
*Petals.*—Texture—medium thickness; strong. Form—ovoid.
*Fragrance.*—Characteristic chrysanthemum.

*Plant*

Form: Upright; branching.
Growth: Vigorous.
Foliage:
*Size.*—Medium.
*Quantity.*—Normal.
*Color.*—Upper side—Dark Yellowish-Green, Plate 18. Reverse side—Light Hellebore Green, Plate 17.
*Texture.*—Leathery.

I claim:

A new and distinct variety of chrysanthemum plant of the decorative class, substantially as herein shown and described, characterized particularly as to novelty by the unique combination of very vigorous, upright and branching habits of growth, a relatively early blooming habit, very good floriferousness, thick flowers, a distinctive and attractive general color tonality of the flowers corresponding to Scarlet, lightly overcast with Scarlet-Red, and good winter hardiness.

No References Cited.

ABRAHAM G. STONE, *Primary Examiner.*